United States Patent [19]

Günther

[11] Patent Number: 4,967,012

[45] Date of Patent: Oct. 30, 1990

[54] ACETALS, AND A PROCESS FOR THE PREPARATION THEREOF

[75] Inventor: Klaus Günther, Eppstein/Taunus, Fed. Rep. of Germany

[73] Assignee: Hoechst Aktiengesellschaft, Frankfurt am Main, Fed. Rep. of Germany

[21] Appl. No.: 357,043

[22] Filed: May 25, 1989

[30] Foreign Application Priority Data

May 28, 1988 [DE] Fed. Rep. of Germany ....... 3818244

[51] Int. Cl.$^5$ ........................................... C07C 49/255
[52] U.S. Cl. ..................................... 568/415; 568/386
[58] Field of Search ......................................... 568/415

[56] References Cited

U.S. PATENT DOCUMENTS 4,825,008  4/1989  Gunther et al. .................... 568/415

FOREIGN PATENT DOCUMENTS 0273378  12/1987  European Pat. Off. ............ 568/415
2022365   8/1969  Fed. Rep. of Germany ...... 568/415

OTHER PUBLICATIONS

S. M. McElvain et al, *J. Am. Chem. Soc.* 74:2662–2667 (1952).
A. N. Nesmeyanov et al, *Chem. Abs.* 55:23335h (1961).
A. N. Nesmeyanov et al, *Chem. Ab.* 55:23336a (1961).

*Primary Examiner*—James H. Reamer

[57] ABSTRACT

The invention relates to acetals of the formula $CH_3-CO-CH=C(OR)_2$ where R is $-(CH_2)_n-OR'$ where n is 2 or 3 and R' is $C_1-C_5$-alkyl.

In addition, the invention relates to a process for the preparation of acetals of the formula $CH_3-CO-CH=C(OR)_2$ where R is $C_1-C_{12}$-alkyl or R is $-(CH_2)_n-OR'$ where n is 2 or 3 and R' is $C_1-C_5$-alkyl. The process comprises reacting diketene with an alcohol of the formula ROH where R has the meaning indicated, in the presence of an acidic catalyst.

3 Claims, No Drawings

ACETALS, AND A PROCESS FOR THE PREPARATION THEREOF

The invention relates to a process for the preparation of acetals of the formula (I)

$$CH_3-CO-CH=C(OR)_2 \qquad (I)$$

where R is $C_1$-$C_{12}$—alkyl or R is —$(CH_2)_n$—OR' where n is 2 or 3 and R' is $C_1$-$C_5$—alkyl. In addition, the invention relates to the novel acetals of the formula (I) where R is —$(CH_2)_n$—OR' where n and R' have the meaning mentioned.

According to the literature, acetylketene diethyl acetal $CH_3$—CO—CH=$C(OC_2H_5)_2$, i.e. the compound of the formula (I) where R is ethyl, is prepared by reacting ketene diethyl acetal with acetyl chloride, but considerable amounts of byproducts are produced in this reaction (McElvain, McShane, J. Am. Chem. Soc. 74, 1952, pages 2662 and 2666). However, the starting substance ketene diethyl acetal is difficult to obtain; its synthesis has many reaction steps, most of which proceed in unsatisfactory yields. Accordingly, this process is not very suitable for the preparation of acetylketene diethyl acetal on a relatively large scale. In addition, only the existence of acetylketene dimethyl acetal is mentioned in the literature (Chem. Abstr., Volume 55, No. 23, 1961, 23335). Acetylketene dialkyl acetals which contain higher alkyl groups than methyl and ethyl are not described in the literature.

Details on the preparation of properties of acetylketene dialkoxyalkyl acetals, ie. compounds of the formula (I) where R is —$(CH_2)_n$—OR' where n is 2 or 3 and R' is $C_1$-$C_5$—alkyl are not found at all in the literature. Recently, a simple process has been found which permits acetylketene dialkyl acetals $CH_3$—CO—CH=$C(OR)_2$ where R is $C_1$-$C_{12}$—alkyl to be obtained (German Patent Application P 3,644,661.0).

In this process, alkyl acetoacetates of the formula $CH_3$—CO—$CH_2$—$COOR^1$ are reacted with an alcohol of the formula $R^2OH$ in the presence of an acidic catalyst to give acetylketene dialkyl acetals of the formula $CH_3$—CO—CH=$C(OR^2)_2$ where $R^2$ can be an alkyl radical having 1 to 12 carbon atoms, and $R^2OH$ is identical with $R^1OH$ or has a higher boiling point than $R^1OH$.

By contrast, the present invention proceeds from diketene instead of from alkyl acetoacetates.

The invention relates to a process for the preparation of acetals of the formula (I)

$$CH_3-CO-CH=C(OR)_2 \qquad (I)$$

where R is $C_1$-$C_{12}$—alkyl or R is —$(CH_2)_n$—OR' where n is 2 or 3 and R' is $C_1$-$C_5$—alkyl, which comprises reacting diketene with an alcohol of the formula ROH where R has the meaning indicated, in the presence of an acidic catalyst. The invention furthermore relates to acetals of the formula (I)

$$CH_3-CO-CH=C(OR)_2 \qquad (I)$$

where R is —$(CH_2)_n$—OR' where n is 2 or 3 and R' is $C_1$-$C_5$—alkyl.

In the process according to the invention, a certain amount of acetoacetate of the formula —$CH_3$—CO—$CH_2$—COOR where R is $C_1$-$C_{12}$—alkyl or R is —$CH_2)_n$-OR' where n is 2 or 3 and R' is $C_1$-$C_5$— alkyl is formed in addition to the desired acetal. The reaction mixture obtained can easily be separated by fractional distillation, the acetal distilling over last as the highest boiling component. The fraction containing the acetoacetate can be rereacted with the appropriate alcohols to form the acetal.

Suitable alcohols ROH for the preparation of the acetals of the formula $CH_2$—CO—CH=$C(OR)_2$ where R is $C_1$-$C_{12}$—alkyl are saturated primary and secondary alcohols having 1 to 12 carbon atoms, preferably having 3 to 6 carbon atoms, where the carbon chain may be straight-chain or branched; saturated primary alcohols are preferably used. The alcohols employed for the preparation of the acetals of the formula $CH_3$—CO—CH=$C(OR)_2$ where R is —$(CH_2)_n$—OR' where n is 2 or 3 and R' is $C_1$-$C_5$—alkyl are ethylene glycol monoalkyl ethers or propylene glycol monoalkyl ethers R'O—$(CH_2)_n$—OH where n is 2 or 3 and the alkyl group R, has 1 to 5 carbon atoms and may be straight-chain or branched. In this formula, n is preferably 2 and R' is preferably $C_1$-$C_3$—alkyl.

1.5 to 6 moles of ROH are preferably employed per mole of diketene. The reaction temperature should be about 110 to 170° C., preferably 130 to 160° C., in order to achieve a sufficiently high reaction rate. When relatively low-boiling alcohols ROH having 1 to 3 carbon atoms are used, it has proven expedient to achieve the reaction temperature of at least 110° C. which is necessary by carrying out the reaction under suitably increased pressure.

The catalysts used are acidic components. Protonic acids, such as sulfuric acid, p-toluenesulfonic acid or phosphoric acid are preferably used. Acidic ion exchangers and molecular sieves are also suitable. The concentration range for the catalyst employed is 0.005 to 5% by weight. When concentrated sulfuric acid is used, a concentration of from 0.05 to 0.2% by weight has proven very favorable.

For the reaction to proceed sufficiently quickly, it is necessary to remove the resultant water of reaction from the system as rapidly and completely as possible. In principle, all suitable methods of water removal from reaction mixtures, such as, for example, azeotropic distillation using an entrainer, can be used for this purpose. In the process according to the invention, it has proven sufficient to support the removal of water during the reaction by passing a gentle stream of nitrogen through the reaction mixture and/or to remove the water of reaction together with excess alcohol.

On an industrial scale, the preparation of the acetals by the process according to the invention can be carried out either batchwise or continuously in a suitable apparatus.

In the case of batchwise production of the acetals, diketene is reacted in a first step with excess alcohol ROH, and the excess alcohol is subsequently removed by vacuum distillation together with the acetoacetate formed at the same time, the acetal formed in this step remaining. In a second step, the acetoacetate removed by distillation is allowed to react with excess alcohol ROH again under the reaction conditions to form the acetal, and the excess alcohol ROH is then removed by vacuum distillation together with the unreacted acetoacetate, the acetal formed in the 2nd step remaining. In order to improve the yield, based on the diketene employed, a further reaction can be carried out, if necessary, with the acetoacetate/excess alcohol mixture removed by distillation in the second step. The acetal formed in the individual steps is combined and purified together by vacuum distillation.

The continuous preparation of the acetal can be carried out in quite an elegant manner in an apparatus which is suitable for this purpose. Diketene is fed into a reactor together with excess alcohol ROH and catalyst. Some of the excess alcohol (together with the water of reaction) is removed in vapor form from the reactor, and the reaction mixture, comprising acetal, acetoacetate and alcohol ROH, is withdrawn in liquid form. The reaction mixture passes into a distillation column, in which the excess alcohol ROH is distilled off at the head together with unreacted acetoacetate. The head product is fed back into the reactor. The impure acetal is removed from the bottom of the column and passed to a further column from which it is distilled off at the head as a pure product. The catalyst and high-boiling residues accumulate in the bottom of this column and are disposed of in a suitable manner.

The acetals which can be prepared by the process according to the invention are compounds which can be employed as starting materials for many syntheses. Due to their constitutuion, they are particularly suitable for cyclization reactions.

Thus, for example, alkoxypyrazoles can be obtained in a simple manner by reacting acetylketene dimethyl acetal with 2-hydrazinopyrimidine (Chemical Abstracts, Vol. 79, 1973, page 388).

It is also known that acetylketene dimethyl acetal and acetylketene diethyl acetal behave as 1-hydroxyvinylketene acetals at certain temperatures and, for example, give anthraquinones substituted in defined positions, which are important as natural dyes (J. Chem. Soc. Perkin Trans. I, 1976, 17, 1872–56).

An analogous situation applies to the other acetals which can prepared according to the invention. The possibility of being able to prepare acetylketene dialkyl acetals and acetylketene dialkoxyalkyl acetals on a relatively large scale in a favorable manner by the process according to the invention opens up a large number of possible syntheses.

The examples below are intended to illustrate the invention. The percentages are percent by weight, unless otherwise specified.

EXAMPLE 1

84 g of diketene were added dropwise over the course of 30 minutes with stirring to 296 g of n-butanol and 0.33 g of concentrated sulfuric acid at 120° C. in a 1 l four-neck flask equipped with stirrer, dropping funnel, thermometer, attached column with condenser and water separator. The vapor phase of the boiling mixture was precipitated in a condenser, the water of reaction was separated off, and the butanol was fed back into the flask. After 2 hours, the 46 g of butanol which had collected in the water separator were replaced by an equal amount of fresh butanol. During the reaction, a gentle stream of nitrogen was passed through the apparatus. After a reaction time of 4 hours, the mixture contained the following components: 205 g of n-butanol, 93 g of butyl acetoacetate, 69 g of acetylketene dibutyl acetal and 4 g of unknown components. If the reaction mixture was allowed to react further, the reaction temperature gradually increased and the alkylketene dibutyl acetal: butyl acetoacetate ratio shifted more and more in favor of the ketene component. After 14 hours, a reaction temperature of 130° C. had been reached, and 183 g of n-butanol, 33 g of butyl acetoacetate, 141 g of acetylketene dibutyl acetal and 11 g of unknown components were present in the mixture. Acetylketene dibutyl acetal was obtained from the reaction mixture by fractional distillation in a purity of 99%.

EXAMPLE 2

In the same apparatus as in Example 1, 84 g of diketene were added dropwise over the course of 10 minutes with stirring to 352 g of n-pentanol and 0.33 g of concentrated sulfuric acid at about 140° C. The water was removed in the same manner as in Example 1. After 2 hours at a reaction temperature of 148° C., the mixture contained the following components: 233 g of n-pentanol, 81 g of pentyl acetoacetate, 103 g of acetylketene dipentyl acetal and 9 g of unknown components. Analogously to Example 1, the acetylketene dipentyl acetal content increased with time and increasing reaction temperature to the detriment of the pentyl acetoacetate proportion. After 13.5 hours, the mixture contained 197 g of n-pentanol, 23 g of pentyl acetoacetate, 188 g of acetylketene dipentyl acetal and 16 g of unknown components at 155° C. Acetylketene dipentyl acetal was obtained from the reaction mixture by fractional distillation in a purity of 99%.

EXAMPLE 3

336 g of diketene were added dropwise over the course of 20 minutes with stirring to 1,216 g of methyl glycol and 1.6 g of concentrated sulfuric acid in a 2 l four-neck flask fitted with stirrer, dropping funnel, thermometer and attached column. During this addition, the temperature increased to about 125° C. In order to remove the resultant water of reaction in a simple manner, methyl glycol was introduced into the flask at a rate of 40 g/h, and evaporated and was withdrawn from the condenser of the apparatus in the same amount. The reaction temperature was a constant 125° C. The reaction was terminated after 15 hours. The mixture contained 960 g of methyl glycol, 179 g of 2-methoxyethyl acetoacetate and 134 g of acetylketene di-2-methoxyethyl acetal. Acetylketene di-2-methoxyethyl acetal was obtained from the mixture by fractional distillation in a purity of 98%.

Determination values: b.p. 10–15° C.; $d_4{}^{20}$ 1.0786; $n_D{}^{20}$ 1.4667.

Elemental analysis calculated: 55.0% C; 8.3% H; 36.7% O; found: 55.1% C; 8.2% H; 36.0% O

EXAMPLE 4

In the same apparatus as in Example 3, 336 g of diketene were added dropwise over the course of 1.5 hours with stirring to 1,440 g of ethyl glycol and 1.8 g of concentrated sulfuric acid. In order to remove the resultant water of reaction, ethyl glycol was introduced into the flask at a temperature of 140 to 145° C. at a rate of 60 g/h, and was evaporated and removed in liquid form from the condenser of the apparatus in the same amount. The reaction was terminated after 18 hours. The mixture contained 1,110 g of ethyl glycol, 170 g of 2-ethoxyethyl acetoacetate and 184 g of acetylketene di-2-ethoxyethyl acetal.

Acetylketene di-2-ethoxyethyl acetal was obtained from the mixture by fractional distillation in a purity of 99%.

Determination values: b.p. 28.7° C.; $d_4{}^{30}$ 1,0250; $n_D{}^{32}$ 1.4564

Elemental analysis calculated: 58.5% C; 8.9% H; 32.5% O; found: 58.2% C; 8.9% H; 32.4% O.

I claim:

1. An acetal of the formula (I)

CH₃—CO—CH=C(OR)₂   (I)

where R is —(CH₂)$_n$—OR' where n is 2 and R' is C₁-C₅—alkyl.

2. An acetal as claimed in claim 1, wherein R' is C₁-C₃—alkyl.

3. An acetal as claimed in claim 2, where n is 2.

* * * * *